US011911021B2

(12) United States Patent
Ozawa et al.

(10) Patent No.: US 11,911,021 B2
(45) Date of Patent: Feb. 27, 2024

(54) METHOD FOR CLOSING WOUND

(71) Applicant: OLYMPUS MEDICAL SYSTEMS CORP., Hachioji (JP)

(72) Inventors: Keita Ozawa, Hino (JP); Kunihide Kaji, Hachioji (JP); Hiroyuki Morishita, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 29 days.

(21) Appl. No.: 17/562,733

(22) Filed: Dec. 27, 2021

(65) Prior Publication Data

US 2022/0202412 A1 Jun. 30, 2022

Related U.S. Application Data

(60) Provisional application No. 63/131,071, filed on Dec. 28, 2020.

(51) Int. Cl.
*A61B 17/00* (2006.01)
*A61B 17/04* (2006.01)
*A61B 17/06* (2006.01)
*A61B 17/22* (2006.01)
A61B 17/062 (2006.01)

(52) U.S. Cl.
CPC .......... *A61B 17/0469* (2013.01); *A61B 17/06* (2013.01); *A61B 2017/00269* (2013.01); *A61B 2017/00818* (2013.01); *A61B 2017/047* (2013.01); *A61B 2017/0496* (2013.01); *A61B 2017/22051* (2013.01)

(58) Field of Classification Search
CPC .............. A61B 17/0469; A61B 17/06; A61B 2017/00818; A61B 2017/047; A61B 2017/0496; A61B 1/00087; A61B 1/273
See application file for complete search history.

(56) References Cited

U.S. PATENT DOCUMENTS

| 10,869,670 | B2* | 12/2020 | Goto ....................... A61B 1/313 |
|---|---|---|---|
| 2007/0129735 | A1* | 6/2007 | Filipi ............. A61B 17/320016 606/144 |
| 2009/0312602 | A1* | 12/2009 | Sakamoto .......... A61B 17/0487 600/114 |
| 2010/0004665 | A1* | 1/2010 | Hong ................. A61B 1/00087 606/148 |
| 2015/0142021 | A1 | 5/2015 | Smith et al. |
| 2019/0290325 | A1* | 9/2019 | Goto .................. A61B 17/3478 |

* cited by examiner

*Primary Examiner* — Katherine M Rodjom
*Assistant Examiner* — Lindsey R. Rivers
(74) *Attorney, Agent, or Firm* — Oliff PLC

(57) ABSTRACT

A method for closing a wound in a tubular organ using a suture thread introduced into the tubular organ, includes: inflating the tubular organ by supplying gas into the tubular organ; resecting a lesion while the tubular organ is inflated, so that the wound is formed; deflating the tubular organ by discharging gas from the tubular organ; passing the suture thread through a tissue around the wound; and gathering the tissue around the wound by pulling the suture thread passing through the tissue while the tubular organ is deflated.

19 Claims, 13 Drawing Sheets

METHOD FOR CLOSING WOUND

CROSS-REFERENCE TO RELATED APPLICATIONS

Priority is claimed on U.S. Patent Application No. 63/131,071, filed on Dec. 28, 2020, the entire content of which is hereby incorporated by reference.

BACKGROUND

Technical Field

The present disclosure relates to a method for closing a wound, more specifically, a method for closing a wound that occurs in a tubular organ under observation with a flexible endoscope.

Background

Endoscopic submucosal dissection (ESD) is becoming widespread as one of the treatments for gastrointestinal tumors. After the ESD procedure, a wider range of mucosal defects than endoscopic mucosal resection (EMR) occurs. From the viewpoint of promoting recovery, it is preferable to close the defective site.

Clips are known as a means for transendoscopically closing a wound such as a mucosal defect, but since the mucosal defect due to ESD is large, it is often impossible to close the wound with a clip.

Another means of closing the wound is suturing with suture threads. By pulling the suture thread around the wound, the peripheries of the wound approach each other and the wound is closed.

Devices for endoscopic suturing have been proposed.

In one device, by pulling in a thread held by a snare or hook and attaching a thread fastener, tissue is sutured by suppressing loosening of the thread passed through the tissue.

SUMMARY

The present disclosure relates to a method for closing a wound in a tubular organ using a suture thread introduced into the tubular organ. The method includes: inflating the tubular organ by supplying gas into the tubular organ; resecting a lesion while the tubular organ is inflated, so that the wound is formed; deflating the tubular organ by discharging gas from the tubular organ; passing the suture thread through a tissue around the wound while the tubular organ is deflated; and gathering the tissue around the wound by pulling the suture thread passing through the tissue while the tubular organ is deflated.

The method for closing a wound according to another aspect of the present disclosure includes: inflating the tubular organ by supplying gas into the tubular organ; resecting a lesion while the tubular organ is inflated, so that the wound is formed; threading the suture thread through a tissue around the wound; deflating the tubular organ by discharging gas from the tubular organ in a state in which the suture thread passes through the tissue around the wound; and gathering the tissue around the wound by pulling the suture thread passing through the tissue while the tubular organ is deflated.

DETAILED DESCRIPTION OF THE PREFERRED EMBODIMENTS

A method for closing a wound according to an exemplary embodiment of the present disclosure (hereinafter, may be simply referred to as "closing method") will be described with reference to FIGS. 1 to 6.

Figure 1:
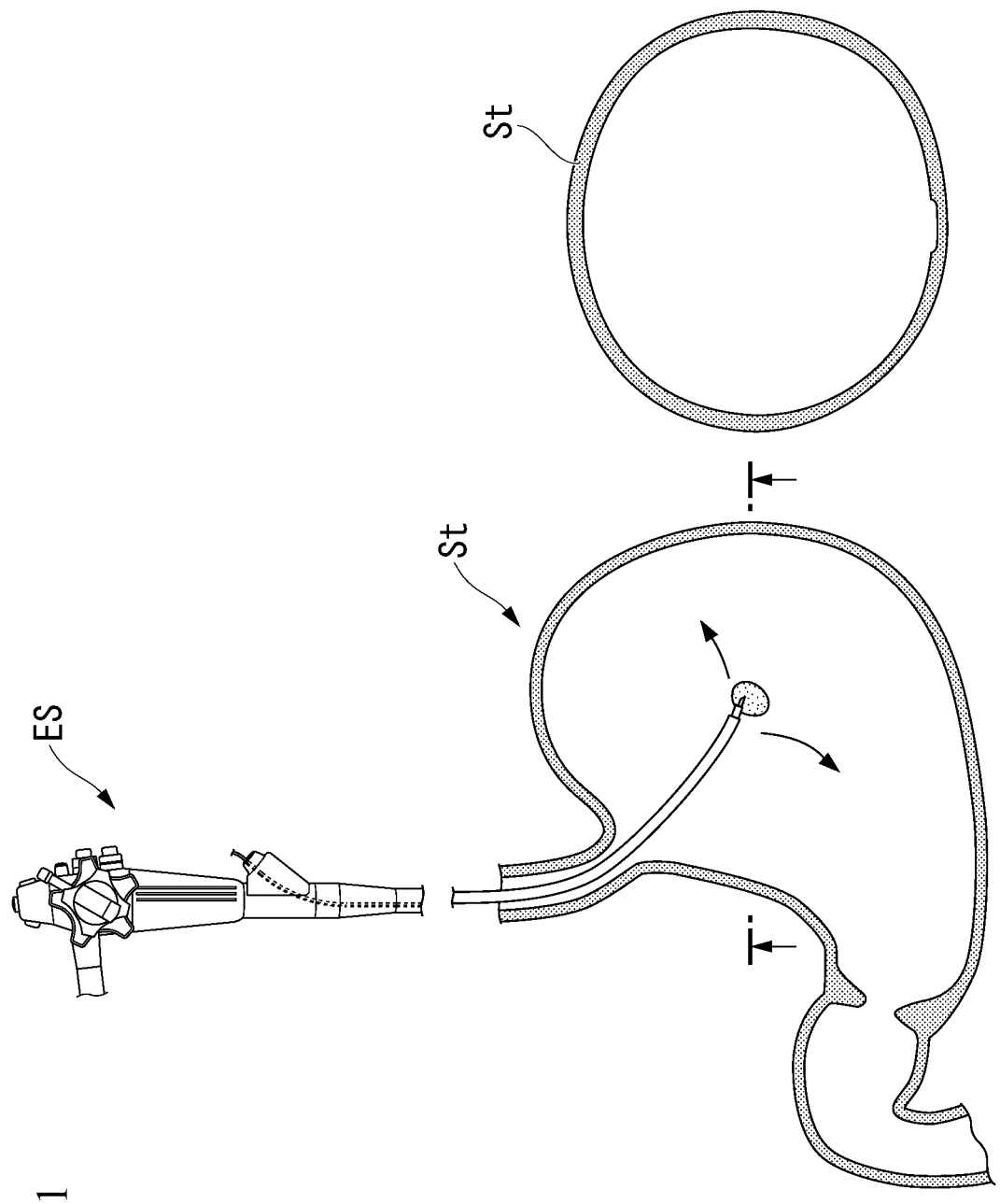
FIG. 1 is a diagram schematically showing a stomach during ESD.

As a preliminary step, a wound to be closed occurs. For example, a flexible endoscope having a flexible insertion portion from the mouth or nose (hereinafter, "endoscope") is inserted into a tubular organ such as the stomach or the large intestine to perform ESD. In ESD, gas is supplied into the tubular organ so that each step can be performed satisfactorily, and a lesion such as a tumor is resected in a state where the tubular organ is inflated. As an example, FIG. 1 schematically shows the stomach St in ESD. The right side of FIG. 1 is a cross-sectional view of the stomach St.

Figure 2:
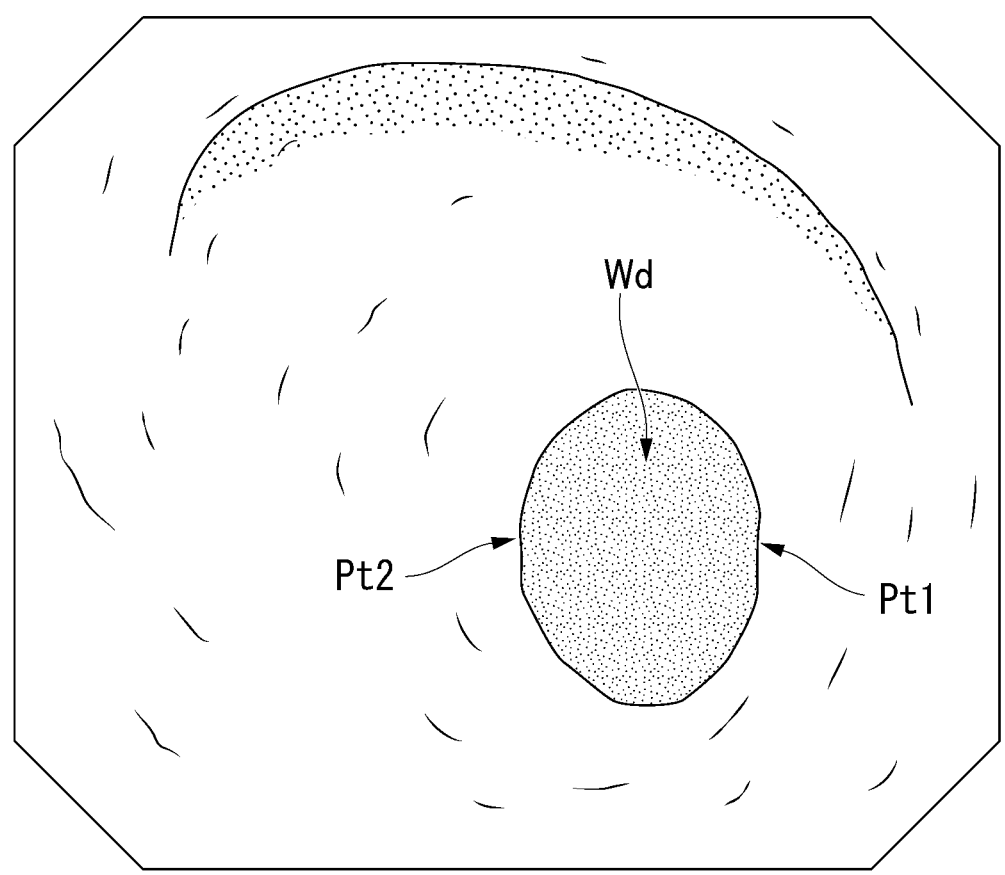
FIG. 2 is a diagram showing an example of a wound that is a target of a method for closing a wound according to the present disclosure.

When the lesion is resected, a relatively large area wound Wd as shown in FIG. 2 occurs at the location of the lesion in the tubular organ.

Figure 3A:
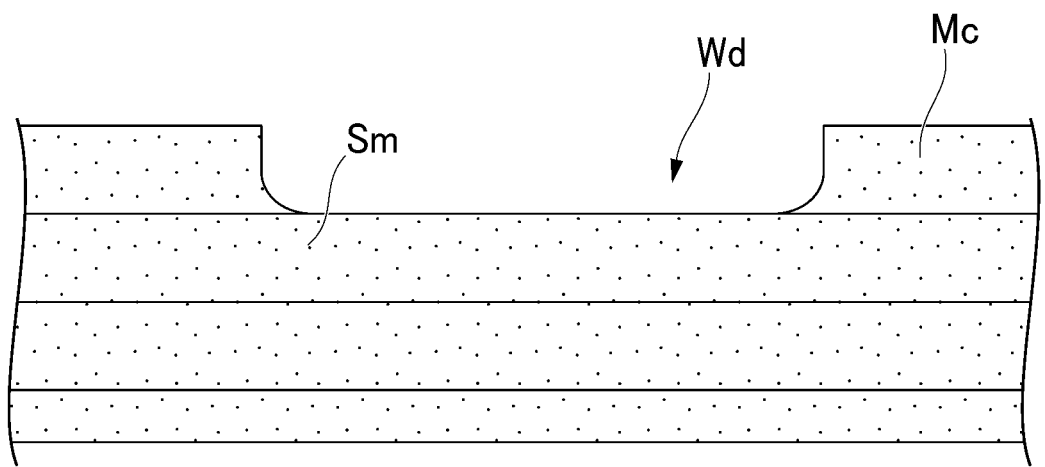
FIG. 3A is a schematic cross-sectional view of the wound.
Figure 3B:
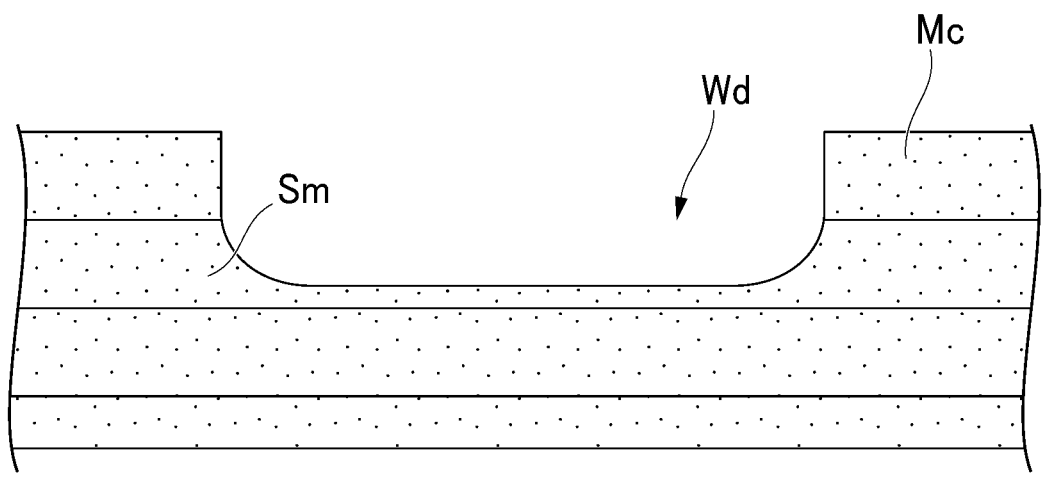
FIG. 3B is another example of a schematic cross-sectional view of the wound.

FIG. 3A shows a schematic cross-sectional view of the wound Wd. In the wound Wd, the mucosal layer Mc is removed and the submucosal layer Sm is exposed. When the lesion reaches a deep position in the submucosal layer, part of the submucosal layer Sm may be removed in the wound Wd as shown in FIG. 3B.

Then, the surgeon closes the wound Wd.

Figure 4:
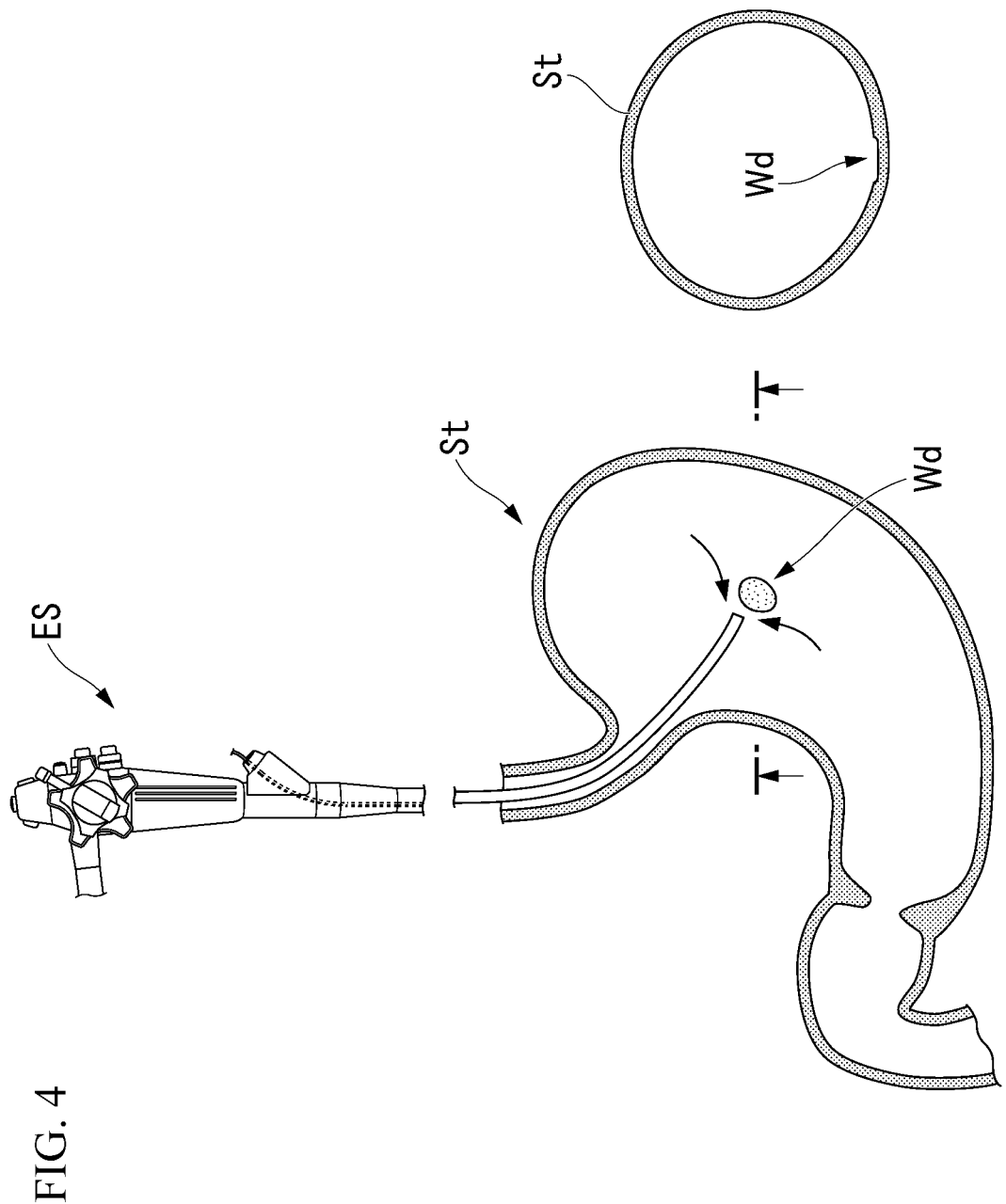
FIG. 4 is a diagram showing an image of a stomach deflated by step A.
Figure 5:
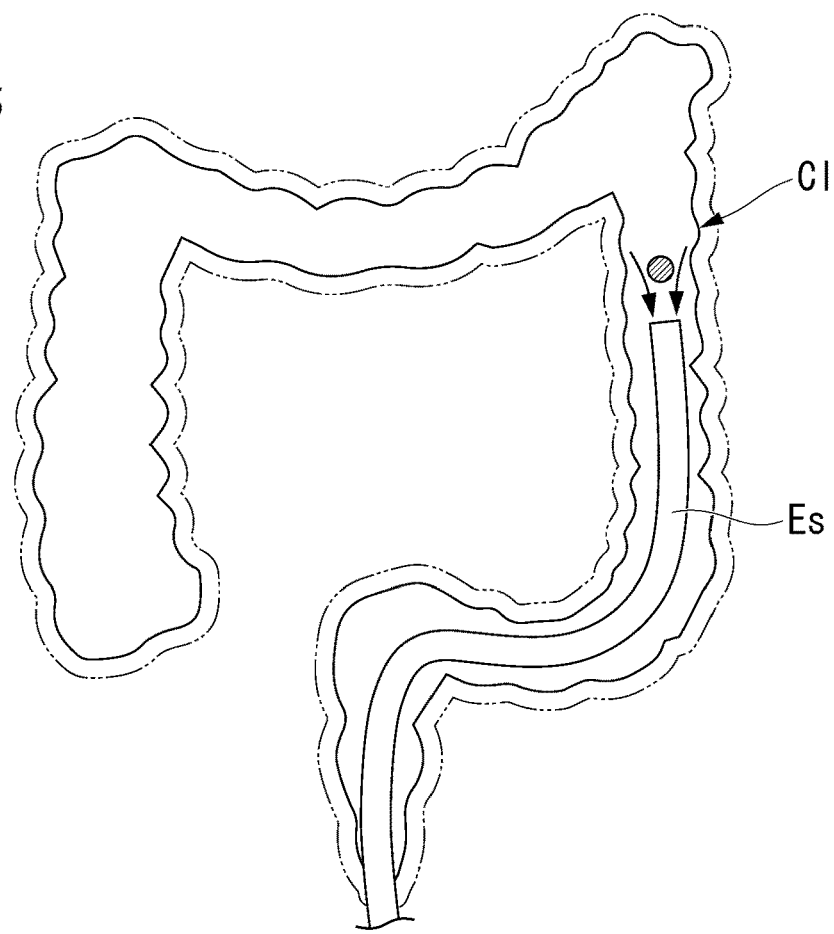
FIG. 5 is a diagram showing an image of a deflated large intestine.

First, the gas in the tubular organ is suctioned and discharged to the outside of the tubular organ to deflate the tubular organ (step A). The image of stomach St after step A is shown in FIG. 4. As another example of a tubular organ, an image of a deflated large intestine Cl is shown in FIG. 5. In FIG. 5, the shape of the large intestine Cl during expansion is shown by a broken line.

It is convenient to discharge the gas using a suction channel provided in the endoscope Es, but it may be performed using a suction tube separately introduced into the tubular organ.

The amount of gas discharged is such that the tubular organ is not occluded, and the gas remains in the tubular organ even when the tubular organ is deflated. In one example, the amount of gas in the tubular organ after the completion of step A is smaller than that in the observation in the tubular organ using an endoscope, and the folds and the like in the tubular organ are not completely extended.

At the end of step A, the extension of the wound Wd and its surrounding tissue is relaxed in the tubular organ. That is, the tension applied to the wound Wd and its surrounding tissues is reduced.

The surgeon projects a needle holder or forceps (hereinafter, "needle holder or the like") inserted into the insertion portion of the endoscope from the distal end of the endoscope. Subsequently, the suture needle introduced into the tubular organ and to which the suture thread is attached is grasped by a needle holder or the like.

Figure 6:
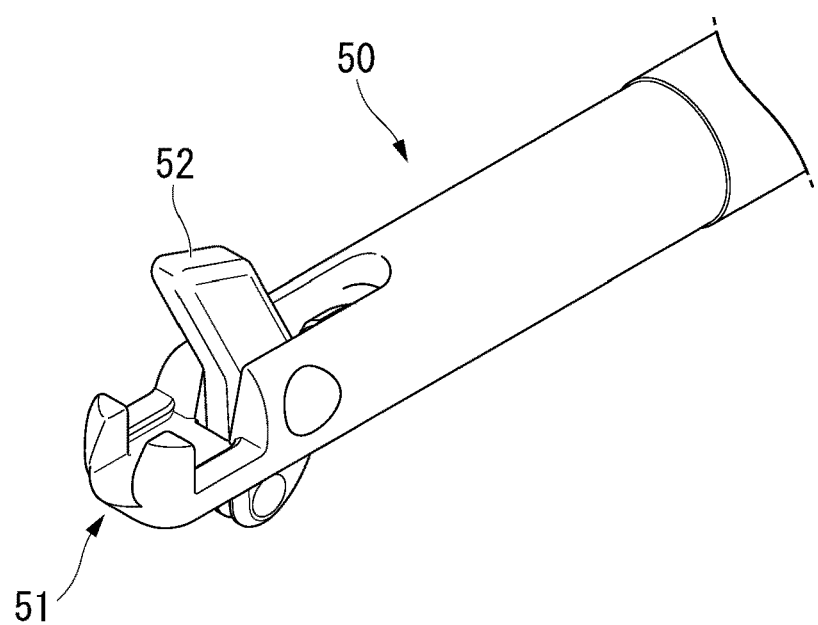
FIG. 6 is a diagram showing an example of a tip portion of a needle holder.

FIG. 6 shows an example of a needle holder. The needle holder 50 shown in FIG. 6 includes a first jaw 51 and a second jaw 52 that rotates with respect to the first jaw 51 at its tip. The needle holder 50 can rotate the second jaw 52 with an operation unit (not shown) at hand, and can grasp a suture needle sandwiched between the first jaw 51 and the second jaw 52. The suture needle and the suture thread may be introduced into the lumen organ by inserting the endoscope while covering the suture needle with an overtube or the like while holding the suture needle with the needle holder 50.

The surgeon passes the suture needle through one peripheral tissue Pt1 (see FIG. 2) of the two peripheral tissues facing each other across the wound Wd, so that a suture thread is passed through the peripheral tissue Pt1 (first position) and locked (first-stage operation). The suture thread is then threaded through the other peripheral tissue Pt2 (see FIG. 2, position 2)(second-stage operation).

Figure 7:
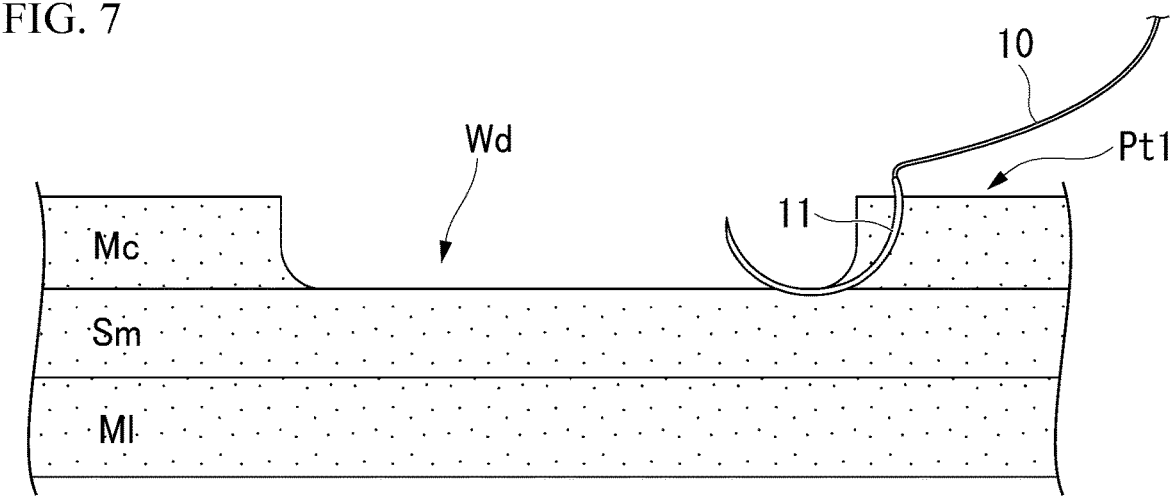
FIG. 7 is a schematic view showing a suture needle passed through a peripheral tissue.

Since the wound generated by ESD is large, in a case where the suture needle is a curved needle of an average size, even if the peripheral tissue Pt1 is pierced and rotated once, the needle tip may not reach the peripheral tissue Pt2 and the needle tip may come out within the range of the wound Wd. In this case, as shown in FIG. 7, the suture needle 11 pierced into the mucosal layer Mc of the peripheral tissue Pt1 is once passed through the submucosal layer Sm and the suture needle 11 is once pulled out from the bottom surface of the wound Wd. After that, the suture needle 11 may be moved to the vicinity of the peripheral tissue Pt2 and pierced into the bottom surface of the wound Wd, and the suture needle 11 and the suture thread 12 may be pulled out from the mucosal layer Mc of the peripheral tissue Pt2 as shown in FIG. 8.

In the first and second stages, the suture needle 11 may pass through the muscular layer Ml beneath the submucosa before exiting the bottom surface of the wound Wd.

Figure 9:
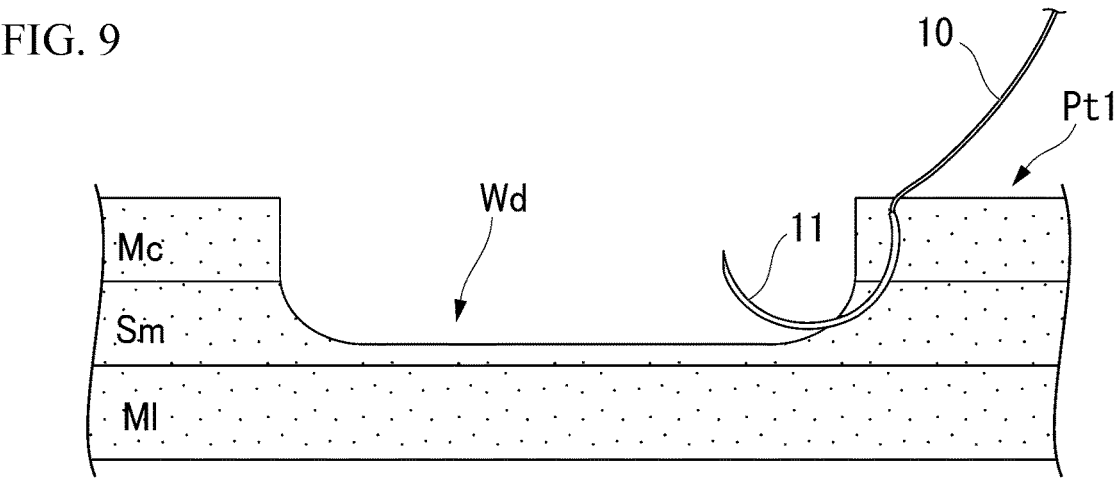
FIG. 9 is a schematic view showing a suture needle passed through a peripheral tissue around another wound.

When the suture thread is passed through a relatively deep wound as shown in FIG. 3B, the suture needle 11 passing through the submucosal layer Sm may come out from the side surface of the wound Wd as shown in FIG. 9.

Figure 8:
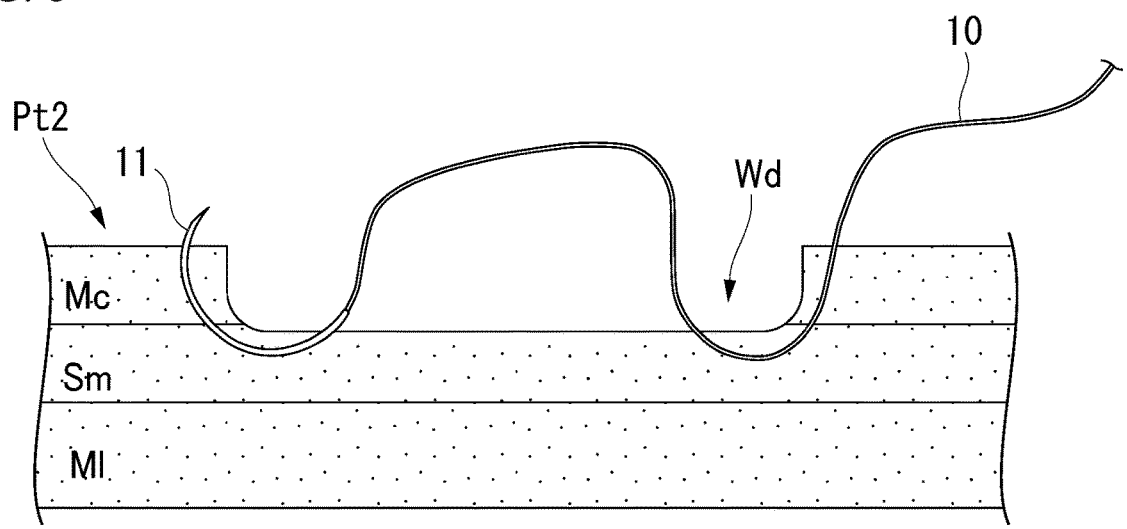
FIG. 8 is a schematic view showing a suture needle passed through a peripheral tissue.
Figure 10:
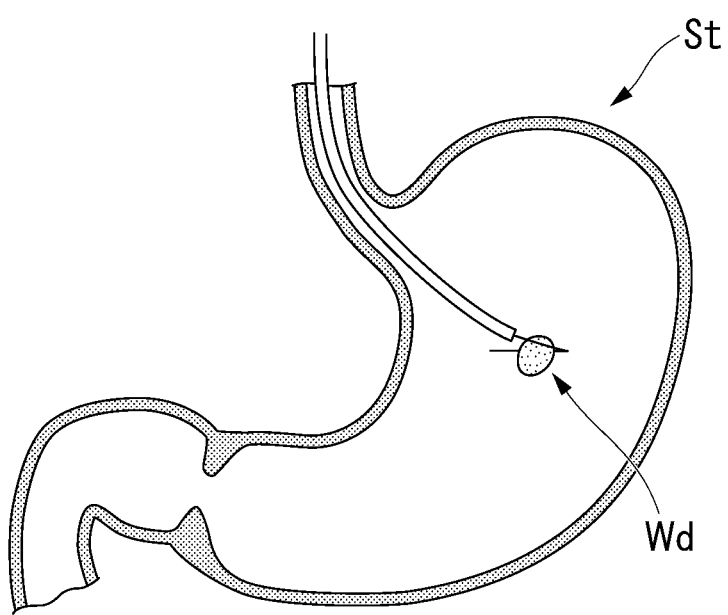
FIG. 10 is a diagram showing an image of the stomach after a first stage operation and a second stage operation.

In the procedure up to this point, as shown in FIG. 8, the suture thread 10 is passed once between the peripheral tissue Pt1 and the peripheral tissue Pt2. The image of the stomach St after the first stage operation and the second stage operation is shown in FIG. 10. The operation of passing the suture thread 10 between the peripheral tissue Pt1 and the peripheral tissue Pt2 once is composed of a set of a first-stage operation and a second-stage operation.

Figure 11:
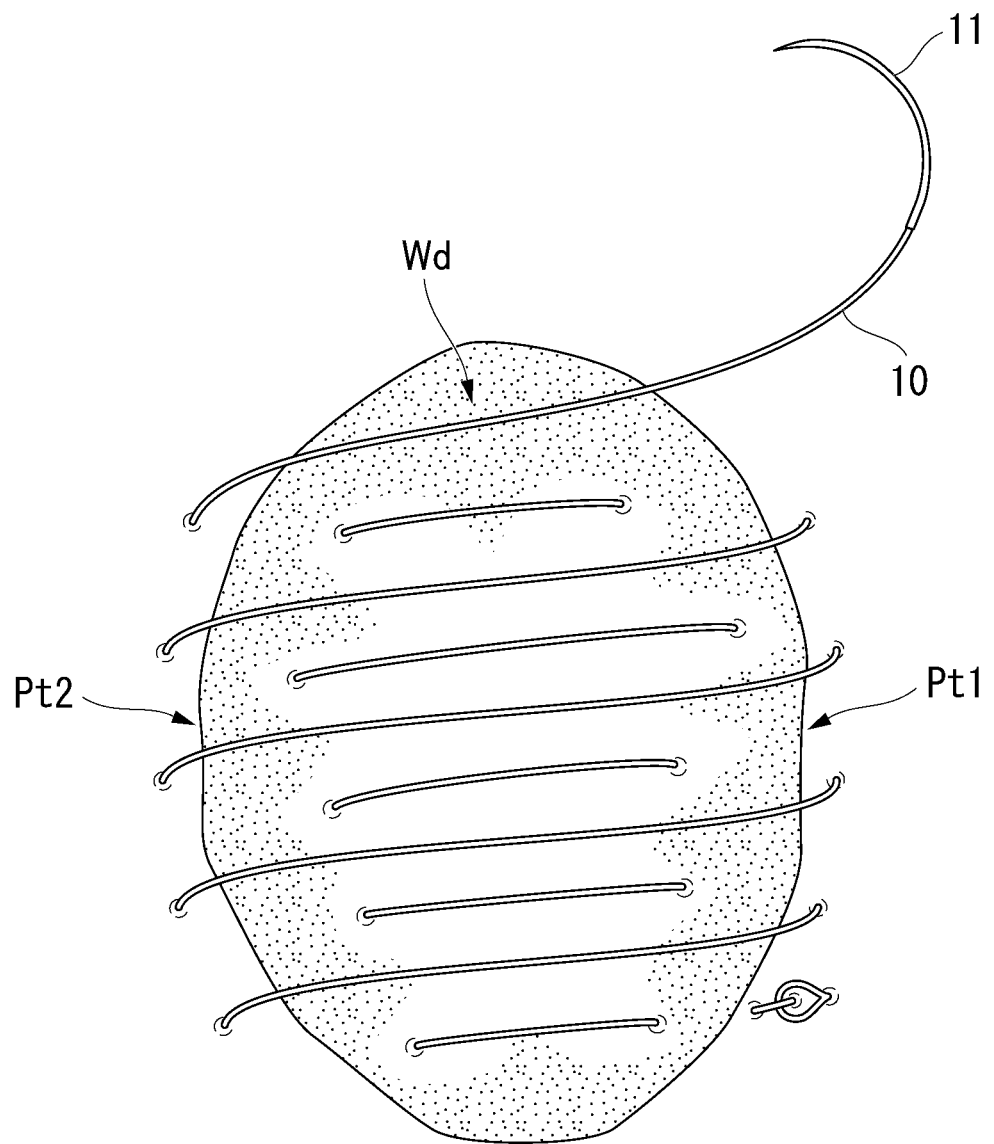
FIG. 11 is a diagram showing the wound after the end of step B.
Figure 12:
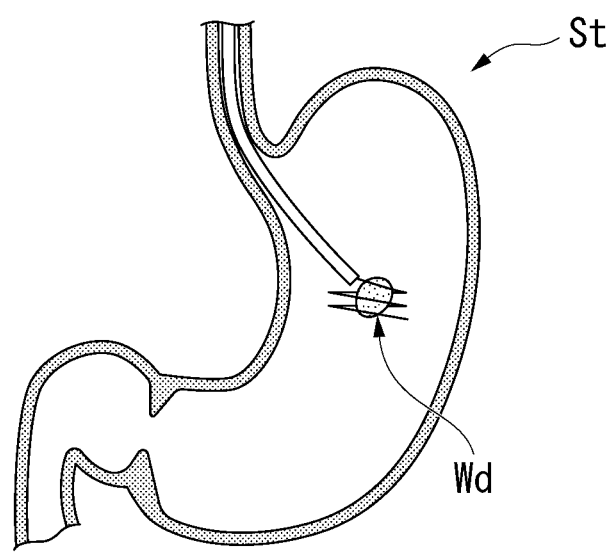
FIG. 12 is a diagram showing an image of the stomach after step B.

The surgeon passes the suture thread 10 through each of the peripheral tissue Pt1 and the peripheral tissue Pt2, then moves the suture needle 11 grasped by the needle holder or the like again to the peripheral tissue Pt1, pierces the suture needle 11 at a different position of the peripheral tissue Pt1, and passes the suture thread 10 through the peripheral tissue Pt1 again. This is repeated a plurality of times depending on the size of the wound Wd, and as shown in FIG. 11, the suture thread 10 is passed a sufficient number of times to close the wound Wd (step B). That is, step B includes a plurality of sets of the first-stage operation and the second-stage operation. The image of the stomach St after step B is shown in FIG. 12.

Figure 13:
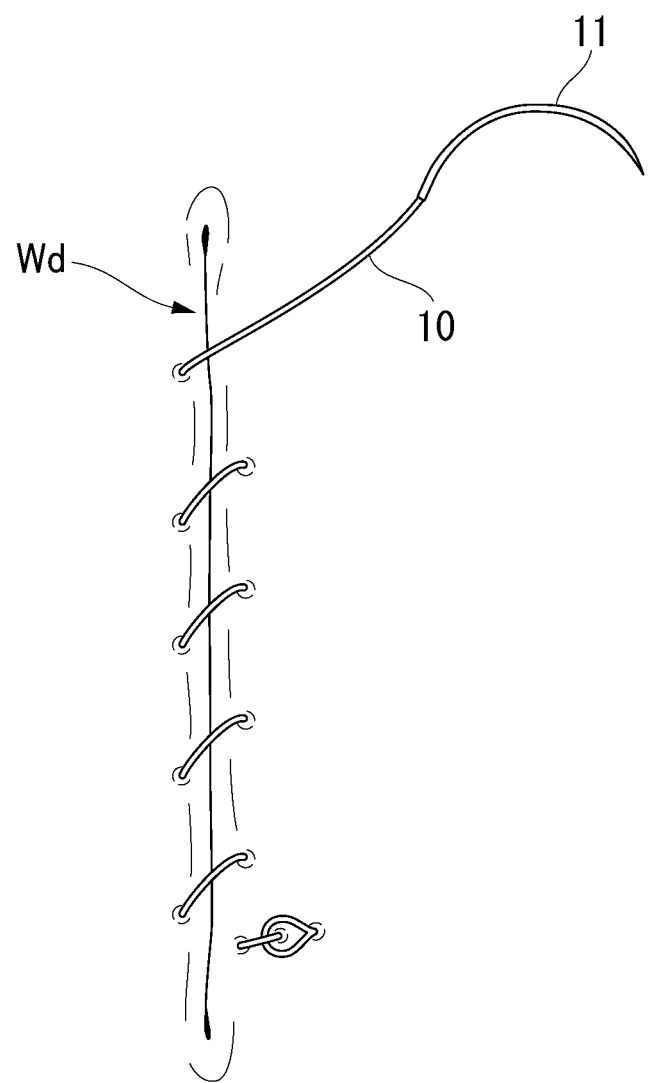
FIG. 13 is a diagram showing a closed wound.

When the suture thread 10 is pulled from the state shown in FIG. 11, the peripheral tissue Pt1 and the peripheral tissue Pt2 approach each other, and the wound Wd is closed as shown in FIG. 13 (step C).

The surgeon cuts the excess suture thread 10 using scissors forceps or the like. After that, the suture needle 11 is taken out of the body to complete a series of procedures.

Figure 14:
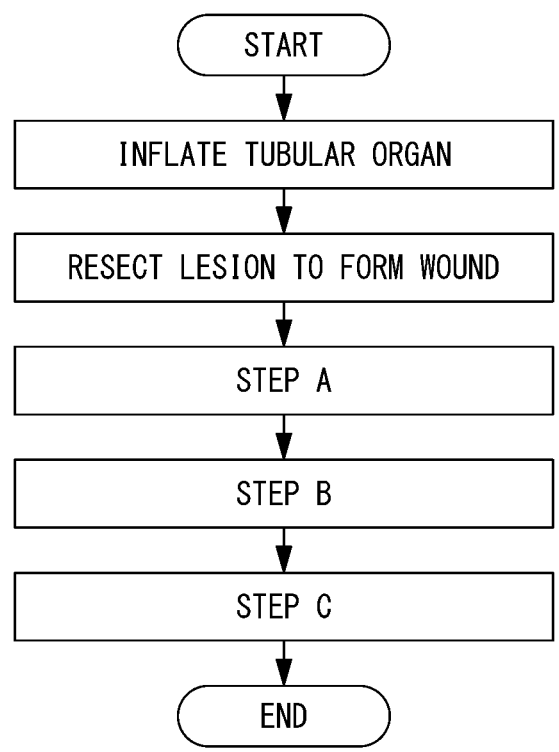
FIG. 14 is a flowchart showing a flow of a method for closing a wound according to an exemplary embodiment.

FIG. 14 shows a flow chart of the method for closing the wound in the present embodiment.

When the wound is closed while the tubular organ is inflated, such as during ESD, the tubular organ will suddenly deflate when the endoscope is removed after the closure is completed, and the tension on the wall of the tubular organ is reduced. As a result, the suture thread that should have been sufficiently pulled when the wound is closed may become loose, and part of the wound may open or a dead space may be generated in the closed wound.

Since the method for closing the wound according to the present embodiment includes step A in which the tubular organ is deflated, the wound is closed in a state where the tubular organ is deflated and the tension is reduced. As a result, after step C of closing the wound, the tension does not decrease sharply, and it is possible to preferably suppress the opening of part of the wound or the formation of a dead space.

Figure 15:
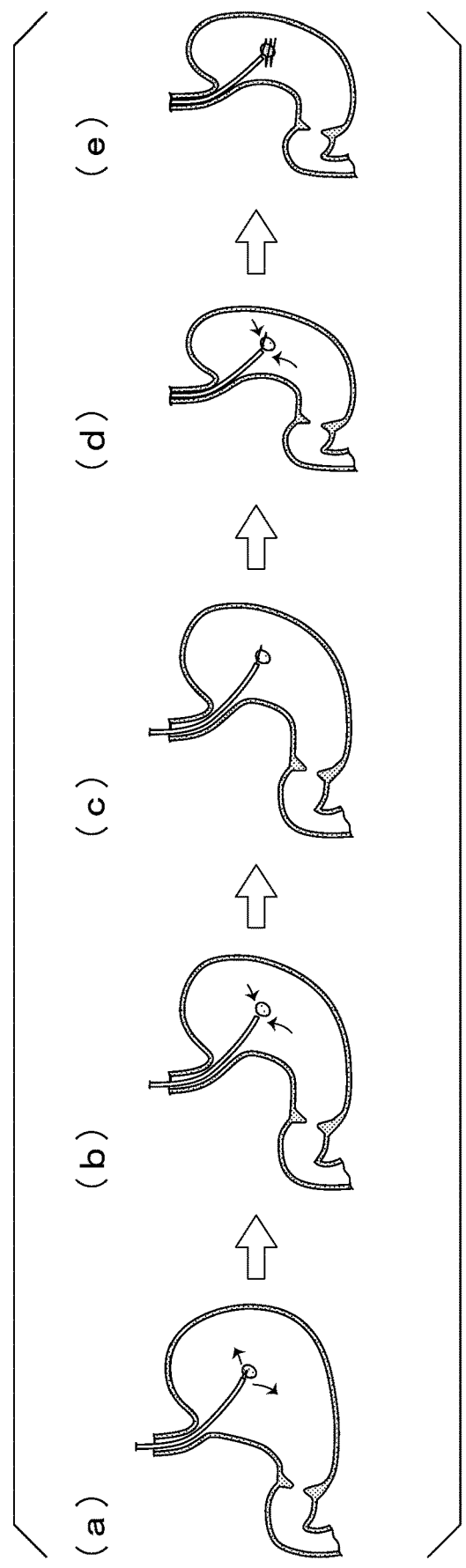
FIG. 15 is a diagram showing the order of a series of procedure steps.

In this embodiment, step A may be performed a plurality of times. For example, the gas in the tubular organ may be further suctioned in the middle of step B after step A. FIG. 15 is a diagram showing the order of a series of procedure steps. In the stomach St, the gas in the tubular organ is further suctioned. By passing the suture thread 10 between the peripheral tissue Pt1 and the peripheral tissue Pt2, the tissue of the tubular organ may be pulled by a small amount and the tension may increase. By further suctioning the gas in the tubular organ in the middle of step B, such an increase in tension can be alleviated, and it is possible to more reliably suppress the opening of part of the wound or the formation of a dead space.

Another exemplary embodiment of the present disclosure will be described with reference to FIG. 16. In the following description, the steps and configurations already described will be designated by the same reference numerals and duplicated description will be omitted as appropriate.

Figure 16:
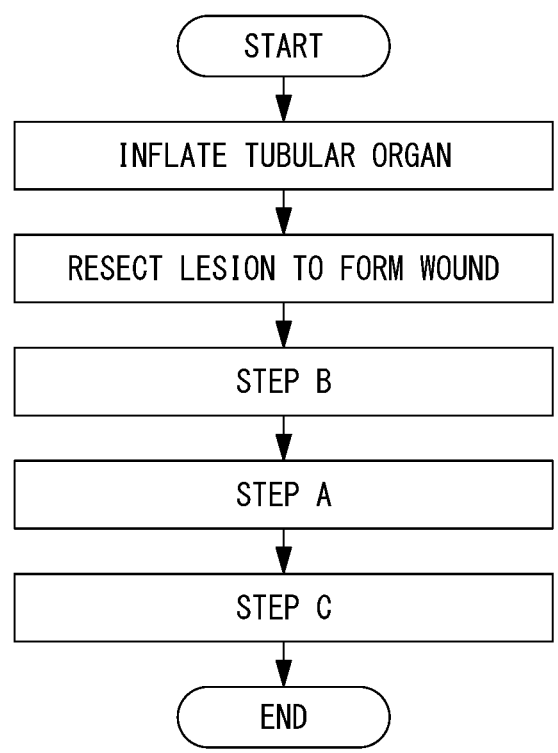
FIG. 16 is a flowchart showing a flow of a method for closing a wound according to an exemplary embodiment.

The flow of the method for closing the wound in this embodiment is shown in FIG. 16 as a flowchart. The flow of the present embodiment is different from the above embodiment only in that step A is performed between step B and step C, and is the same in other respects.

That is, after the suture thread 10 has been passed a sufficient number of times to close the wound Wd, the gas in the tubular organ is aspirated.

Also in this embodiment, since the suture thread 10 is pulled and the wound is closed while the tubular organ is deflated, the tension does not decrease sharply after step C. Therefore, as in the above embodiment, it is possible to preferably suppress the opening of part of the wound or the formation of a dead space.

In this embodiment, step A may be performed in the middle of step B. For example, step A may be performed when the suture thread 10 is passed between the peripheral tissue Pt1 and the peripheral tissue Pt2 a predetermined number of times or more. Further, step A may be performed during the first-stage operation and the second-stage operation in the process of passing the suture thread 10 between the peripheral tissue Pt1 and the peripheral tissue Pt2.

Step A may be performed twice or more in the middle of step B, or may be performed both in the middle of step B and after the end of step B.

Although each embodiment of the present disclosure has been described above, the technical scope of the present disclosure is not limited to the above-described embodiments, and it is possible to change the combination of components, make various changes to each component, and delete them without departing from the spirit of the present disclosure.

The wounds that are closed in the present disclosure are not limited to those that occur after lesion resection by ESD. Therefore, the method for closing the wound according to the present disclosure can be widely applied to all the wounds generated in the tubular organ. For example, a wound that occurs by EMR in which the snare wire is resected over the mucous membrane, a wound that occurs by a disease such as a gastric ulcer, and the like can be mentioned.

What is claimed is:

1. A method for closing a wound in a tubular organ using a suture thread introduced into the tubular organ, the method comprising:
    inflating the tubular organ by supplying gas into the tubular organ;
    resecting a lesion while the tubular organ is inflated, so that the wound is formed;
    discharging gas from the tubular organ to contract an entirety of the tubular organ;
    passing the suture thread through a tissue around the wound while the entirety of the tubular organ is contracted; and
    gathering the tissue around the wound by pulling the suture thread passing through the tissue while the entirety of the tubular organ is contracted.

2. The method according to claim 1, wherein the gas is discharged from the tubular organ by using an endoscope inserted in the tubular organ.

3. The method according to claim 1, wherein the passing of the suture thread through the tissue around the wound includes a first-stage operation of passing the suture thread through the tissue at a first position and a second-stage operation of passing the suture thread through the tissue at a second position different from the first position, and
    the tubular organ is further contracted by discharging gas from the tubular organ during the first-stage operation and the second-stage operation.

4. The method according to claim 1, wherein the passing of the suture thread through the tissue around the wound includes a first-stage operation of passing the suture thread through the tissue at a first position and a second-stage operation of passing the suture thread through the tissue at a second position facing the first position across the wound,
    a set of the first-stage operation and the second-stage operation is performed twice or more, and
    gas is discharged from the tubular organ between successive sets of the first-stage operation and the second-stage operation.

5. The method according to claim 1, further comprising:
    contracting the tubular organ by further discharging gas from the tubular organ to form a second contracted state after the suture thread has passed through the tissue around the wound,
    wherein the contraction of the tubular organ before the passing of the suture thread through the tissue around the wound forms a first contracted state; and
    the suture thread is passed through the tissue around the wound while the tubular organ is in the first contracted state.

6. The method according to claim 1, wherein the tubular organ is a stomach.

7. The method according to claim 1, wherein the tubular organ is a large intestine.

8. The method according to claim 1, wherein the wound is formed by removing a mucosal layer during the resecting, and
    a submucosa of the wound is exposed.

9. The method according to claim 1, wherein the threading of the suture thread through the tissue around the wound includes:
    after passing a suture needle pierced into a mucosal layer of the tissue through a submucosal layer, pulling out the suture needle from a bottom surface of the wound; and
    after the suture thread is pierced into the bottom surface, pulling out the suture needle and the suture thread from the mucosal layer of the tissue.

10. The method according to claim 1, wherein the passing of the suture thread through the tissue around the wound includes:
    penetrating a region between the wound and a mucosal layer of the tissue around the wound with a suture needle held by a needle holder protruding from a distal end of an endoscope.

11. A method for closing a wound in a tubular organ using a suture thread introduced into the tubular organ, the method comprising:
    inflating the tubular organ by supplying gas into the tubular organ;
    resecting a lesion while the tubular organ is inflated, so that the wound is formed;
    threading the suture thread through a tissue around the wound;
    deflating the tubular organ by discharging gas from the tubular organ in a state in which the suture thread passes through the tissue around the wound; and
    gathering the tissue around the wound by pulling the suture thread passing through the tissue while the tubular organ is deflated.

12. The method according to claim 11, wherein the suture thread is passed through the tissue around the wound while the tubular organ is inflated.

13. The method according to claim 11, wherein the gas is discharged from the tubular organ by using an endoscope inserted into the tubular organ.

14. The method according to claim 11, wherein the threading of the suture thread through the tissue around the wound includes a first-stage operation of passing the suture thread through the tissue at a first position and a second-stage operation of passing the suture thread through the tissue at a second position facing the first position across the wound, a set of the first-stage operation and the second-stage operation is performed twice or more, and gas is discharged from the tubular organ between successive sets of the first-stage operation and the second-stage operation.

15. The method according to claim 11, wherein the tubular organ is a stomach.

16. The method according to claim 11, wherein the tubular organ is a large intestine.

17. The method according to claim 11, wherein the wound is formed by removing a mucosal layer during the resecting, and a submucosa of the wound is exposed.

18. The method according to claim 11, wherein the threading of the suture thread through the tissue around the wound includes:

after passing a suture needle pierced into a mucosal layer of the tissue through a submucosal layer, pulling out the suture needle from a bottom surface of the wound; and after the suture thread is pierced into the bottom surface, pulling out the suture needle and the suture thread from the mucosal layer of the tissue.

19. The method according to claim 11, wherein the threading of the suture thread through the tissue around the wound includes:

penetrating a region between the wound and a mucosal layer of the tissue around the wound with a suture needle held by a needle holder protruding from a distal end of an endoscope.

* * * * *